Figure 1:
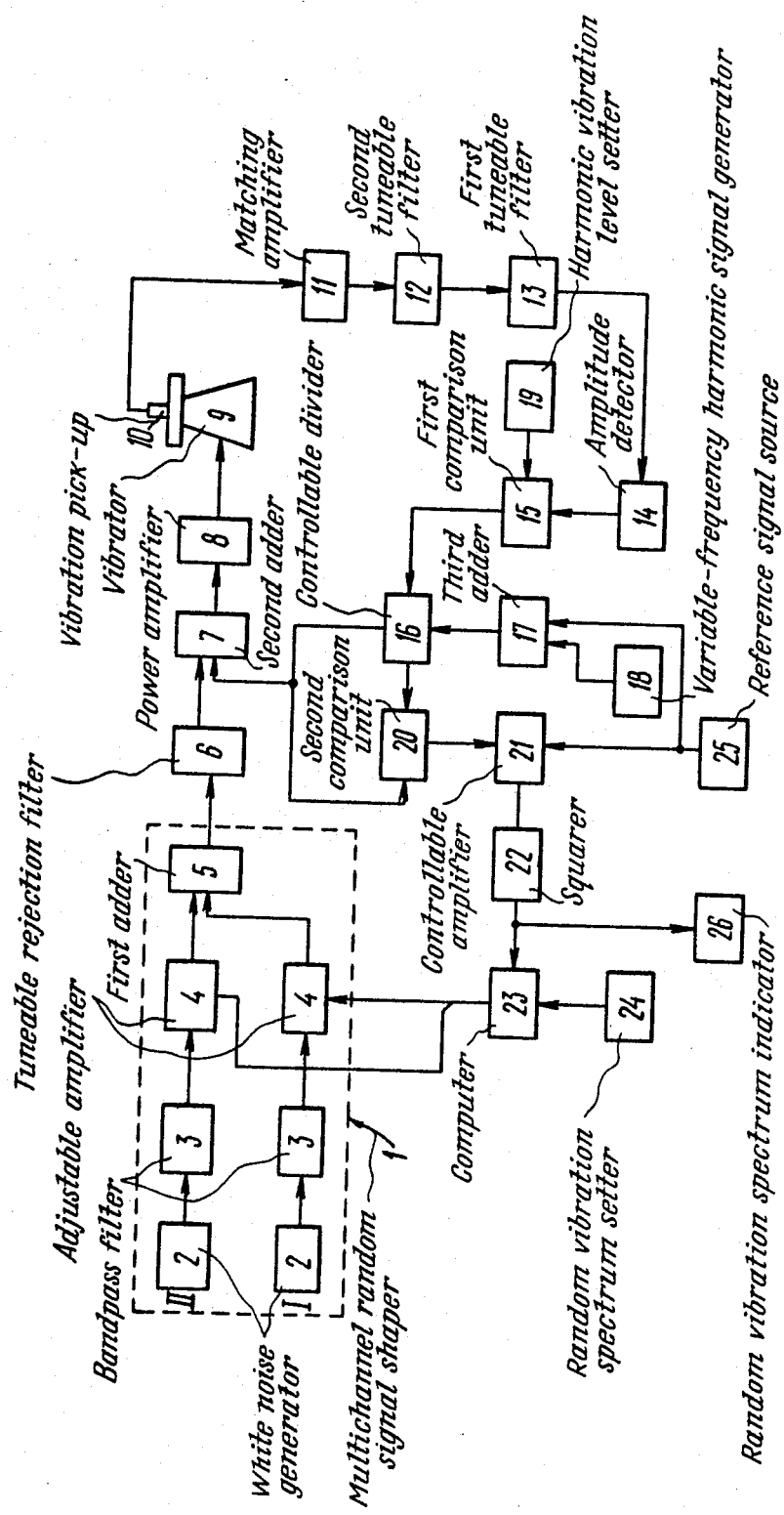

United States Patent [19]

Uretsky et al.

[11] Patent Number: 4,513,620
[45] Date of Patent: Apr. 30, 1985

[54] SYSTEM FOR TESTING ARTICLES WITH RANDOM AND HARMONIC VIBRATIONS

[75] Inventors: Yan S. Uretsky; Rashid R. Kajumov; Zaur A. Bashirov; Alfia G. Bashirova; Alexandr A. Strelnikov, all of Kazan, U.S.S.R.

[73] Assignee: Kazansky Aviatsionny Institut Imeni A. N. Tupoleva, U.S.S.R.

[21] Appl. No.: 522,385

[22] Filed: Aug. 12, 1983

[51] Int. Cl.³ .............................................. G01M 7/00
[52] U.S. Cl. ..................................................... 73/664
[58] Field of Search ........................... 73/664; 364/508

[56] References Cited

U.S. PATENT DOCUMENTS 3,157,045 11/1964 Maki ....................................... 73/664
3,710,082 1/1973 Sloane et al. ........................ 73/664
3,848,115 11/1974 Sloane et al. ........................ 73/664

FOREIGN PATENT DOCUMENTS 938054 6/1982 U.S.S.R. ................................ 73/664

Primary Examiner—Howard A. Birmiel
Assistant Examiner—John E. Chapman, Jr.
Attorney, Agent, or Firm—Steinberg & Raskin

[57] ABSTRACT

A system for testing articles with random and harmonic vibrations comprises a multichannel random signal shaper, a tuneable rejection filter connected to the output of the shaper, a vibrator connected to the output of the filter through an adder and a power amplifier which are placed in series, first and second tuneable filters and a signal spectrum analyzer connected to the first tuneable filter. The system according to the invention includes a variable-frequency harmonic signal generator, the signal spectrum analyzer representing a harmonic signal analyzer and comprising a harmonic signal control loop and a random signal control loop coupled thereto.

4 Claims, 2 Drawing Figures

SYSTEM FOR TESTING ARTICLES WITH RANDOM AND HARMONIC VIBRATIONS

FIELD OF THE INVENTION

The present invention relates to devices designed to test various articles for mechanical effects and in particular to vibration testers. More specifically, it concerns systems for testing articles with harmonic and random vibration.

The system in compliance with the invention may be used for testing articles with random vibration in a predetermined spectrum, harmonic vibrations of an exceedingly low level being used for controlling random vibration parameters.

BACKGROUND ART

There is known a system (cf. A. A. Kuznetsov "Vibration Tests of Automatic Elements and Devices", Moscow, "Energy" publishers, 1976, p. 107, in Russian) for testing articles with wide-band random vibrations by scanning a random narrow-band signal in a predetermined frequency range, said method enabling tests of articles by affecting them with a scanning harmonic signal also in a predetermined frequency range. The system comprises such series-connected components as a white-noise generator, a narrow-band filter, a balanced modulator having its second input connected to a crystal oscillator, an adjustable amplifier having its second input connected to such series-connected components as an amplifier and a detector of the automatic gain control circuit, a mixer having its second input connected to a variable-frequency oscillator, and an output amplifier connected to the input of a vibrator and to the input of a voltmeter.

The narrow-band filter may be transferred to the harmonic signal generating mode for testing articles with harmonic vibration.

The aforesaid system has been open to the objection that it is generally impossible, firstly, to produce wide-band random vibrations throughout the preset frequency range and, secondly, to perform tests with mixed harmonic and random vibrations.

There is also known a system (cf. relevant publication by Brüel & Kjaer, Denmark) for testing articles with mixed harmonic and random vibrations comprising a multichannel random signal shaper wherein each channel includes such series-connected components as a noise generator, a bandpass filter and an adjustable amplifier, the output of each channel being connected to one of the inputs of an adder, and a vibrator with a vibration pick-up for converting mechanical oscillations into an electrical signal, which is connected to the multichannel random signal shaper through such series-connected components as a second adder and a power amplifier. The output of the vibration pick-up is connected through a matching amplifier to the input of a tuneable filter having two outputs, one of which (namely, the suppression output) is connected via a multichannel random signal spectrum analyzer to the adjustable amplifier of each channel of the multichannel shaper, while the other output is connected to the control input of a harmonic signal generator whose harmonic tuning frequency corresponds to the tuning frequency of said tuneable filter, the output of said generator being connected to the input of the second adder.

The system under review permits testing articles simultaneously with harmonic and random vibrations. However, as a harmonic signal is automatically passed through a predetermined frequency range, there occurs synchronous tuning of the tuneable filter whose suppression output is connected to the input of the random signal spectrum analyzer. Consequently, the multichannel random signal spectrum analyzer will measure a decreased value in the nth channel instead of true variance of a random signal, $D_n$, said signal being formed by the multichannel random signal shaper in the nth channel. The above condition is caused by the need to suppress a harmonic signal by $\Delta D_n$, which indicates a shaping error in the random variation spectrum in the nth band of the predetermined frequency range. Said shaping error will result in increased vibrations.

Another disadvantage of the aforesaid system is a large measuring error and, in effect, an appreciable error in setting a harmonic signal level due to the fact that the random signal spectrum overlap, particularly when the random signal is commensurable with the harmonic signal level or exceeds it. Moreover, the random signal level is channels of the random signal shaper is controlled with due account taken of the results obtained in measuring spectral density of the random signal, which gives rise to a statistical analysis error $$\epsilon = \frac{1}{\sqrt{T \cdot \Delta f}},$$

where T is the analysis time determined by parameters of the random signal spectrum analyzer and $\Delta f$ is the band wherein the frequencies are analyzed. Decreasing $\epsilon$ increases an analysis time, a disadvantage substantially increasing the time required to tune the multichannel random signal shaper.

DISCLOSURE OF THE INVENTION

A primary object of the invention is to create a system for testing articles with random and harmonic vibration, which would permit obtaining a wider dynamic range wherein vibrations are set up.

Another primary object of the invention is to provide a system for testing articles with random and harmonic vibration, which would make it possible to increase accuracy and response in tuning the system to a predetermined random vibration spectrum.

One more object of the invention is to create a system for testing articles with random and harmonic vibration, which would enable measurements of random vibration parameters by the use of a conventional amplitude detector having a small constant of integration.

A further object of the invention is to create a system for testing articles with random and harmonic vibration, which would permit eliminating mutual influence of bandpass filters of a multichannel shaper.

A still another object of the invention is to enable utilization of simple, widely known standard structural elements and to appreciably simplify the entire system.

A still further object of the invention is to create a system for testing articles with random and harmonic vibration, which would allow eliminating multichannel feedback and ensure system stability.

One more object of the invention is to provide a random vibration spectrum shaper, which would permit eliminating mutual influence of bandpass filters of a multichannel shaper.

The foregoing and other objects of the invention are accomplished by that a system for testing articles with random and harmonic vibration comprising a multichannel random signal shaper wherein each channel includes a white noise generator, a bandpass filter and an adjustable amplifier, the output of each channel, characterized by an intrinsic amplitude-frequency response, being connected to one of the inputs of a first adder, a vibrator with a vibration pick-up for converting mechanical oscillations into an electrical signal connected to the multichannel random signal shaper through such series-connected components as a second adder and a power amplifier, the output of the vibration pick-up being connected through a matching amplifier to the input of a first tuneable filter having two outputs, one of which (namely, the suppression output) is connected via a signal spectrum analyzer to the adjustable amplifier of each channel of the multichannel shaper, while the other output thereof is connected to a harmonic signal generator whose harmonic tuning frequency corresponds to the tuning frequency of said first tuneable filter, the output of said generator being connected to the second input of a second adder, which, according to the invention, includes a rejection filter tuned in synchronism with the first tuneable filter and inserted between the first and second adders, and a second filter tuned in synchronism with the first tuneable filter having a reverse amplitude-frequency response with respect to the amplitude-frequency response of the rejection filter and inserted between the matching amplifier and the first tuneable filter, which eliminates overlap of the harmonic and random signal spectra.

Advantageously the signal spectrum analyzer represents a harmonic signal analyzer and comprises a harmonic signal control loop including such series-connected components as an amplitude detector, a first comparison unit having its second input connected to a harmonic vibration level setter and a controllable divider having a sum signal output and a signal AC component output connected to the second adder, the input of the amplitude detector being connected to the output of the first tuneable filter, while the second input of the controllable divider is connected to the output of the variable-frequency harmonic signal generator through a third adder having its second input connected to a reference signal source, and a random signal control loop incorporating such series-connected components as a second comparison unit having its one input connected to the sum signal output of the controllable divider and its other input coupled to the signal AC component output of the controllable divider, a controllable amplifier, a squarer and a computer whose second input is connected to a random vibration spectrum setter, while the output of the computer is connected to the adjustable amplifier of each channel of the multichannel random signal shaper, the reference signal source being also connected to the second input of the controllable amplifier, the output of the squarer being also connected to a random vibration spectrum indicator.

The system forming the subject of the present invention permits increasing accuracy and response in producing random vibrations owing to control of the adjustable amplifier of each channel of the multichannel random signal shaper based on the results obtained in processing a harmonic signal. This eliminates the need for high stability, identity and squareness of amplitude-frequency characteristics of like channels comprised in the multichannel shaper and random signal analyzer.

BRIEF DESCRIPTION OF THE ACCOMPANYING DRAWINGS

The invention will now be described further with reference to a specific embodiment thereof, taken in conjunction with the accompanying drawings, wherein:

FIG. 1 is a block diagram of a system for testing articles with random and harmonic vibration according to the invention; and FIG. 2 is a functional diagram of the system for testing articles with random and harmonic vibration according to the invention.

BEST MODE OF CARRYING OUT THE INVENTION

Referring initially to FIG. 1 the system for testing articles with random and harmonic vibration forming the subject of the present invention comprises a multichannel random signal shaper 1 wherein each channel generates a random narrow-band signal and includes such series-connected components as a white noise generator 2, a bandpass filter 3, and an adjustable amplifier 4. The output of each adjustable amplifier 4 is connected to a respective input of a first adder 5. To enable better understanding of the described system for testing articles with random and harmonic vibration, the block diagram of FIG. 1 shows the multichannel shaper 1 having only two channels I and II.

The output of the adder 5 is connected to a vibrator 9 with a vibration pick-up 10 through such series-connected components as a rejection filter 6, a second adder 7, and a power amplifier 8. The proposed system also comprises a signal spectrum analyzer representing a harmonic signal analyzer incorporating a harmonic signal control loop and a random signal control loop. The output of the vibration pick-up 10 is connected to the control input of a controllable divider 16 via such series-connected components as a matching amplifier 11, a second tuneable filter 12 having a reverse amplitude-frequency response with respect to the amplitude-frequency response of the rejection filter 6, a first tuneable filter 13, an amplitude detector 14, and a first comparison unit 15, a second input of said controllable divider being connected through a third adder 17 to a variable-frequency harmonic signal generator 18 tuned in synchronism with the tuning frequency of the tuneable filter 13. A harmonic vibration level setter 19 is connected to the second input of the first comparison unit 15.

The harmonic signal control loop incorporates the amplitude detector 14, the first comparison unit 15, the harmonic vibration setter 19, and the controllable divider 16.

The signal AC component output of the controllable divider 16 is connected to the second input of the second adder 7 and to the first input of a second comparison unit 20 whose second input is connected to the sum signal output of the controllable divider 16. The output of the second comparison unit 20 is connected to the adjustable amplifier 4 of each channel of the multichannel shaper 1 through such series-connected components as a controllable amplifier 21, a squarer 22 and a computer 23. A random vibration spectrum setter 24 is connected to the second input of the computer 23, a reference signal source 25 being connected to the second input of the third adder 17 and to the second output of the controllable amplifier 21, while the output of the squarer 22 is also connected to a random vibration spectrum indicator 26.

The random signal control loop incorporates the second comparison unit 20, the controllable amplifier 21, the squarer 22, the computer 23, as well as the random vibration spectrum setter 24 and the indicator 26.

The system for testing articles with random and harmonic vibration forming the subject of the present invention operates as follows.

A random wide-band signal having a uniform spectrum in a predetermined frequency range is applied from the output of each noise generator 2 to the input of the band-pass filter 3, a random narrow-band signal being delivered from the output of said bandpass filter through the adjustable amplifier 4 to the input of the first adder 5. From the output of the adder 5, that is, from the output of the multichannel random signal shaper a random wide-band signal determining a spectrum of random vibrations applied to an article under test (not shown in FIG. 1) comes to the input of the tuneable rejection filter 6.

The output signal of the tuneable rejection filter 6 is applied to the input of the second adder 7 whose other input accepts the output signal of the harmonic signal generator 18 through the third adder 17 and the adjustable divider 16. The output signal of the second adder 7 being a sum of the random wide-band signal and the harmonic signal is delivered through the power amplifier 8 to the input of the vibrator 9 with the vibration pick-up 10. The signal picked off from the vibration pick-up 10 is fed through the matching amplifier 11 to the input of the second tuneable narrow-band filter 12 having a reverse amplitude-frequency response with respect to the amplitude-frequency response of the tuneable rejection filter 6. From the output of the second tuneable filter 12 the signal whose spectrum includes a random wide-band signal and a harmonic amplified by many times comes to the input of the first tuneable filter 13 which extracts a harmonic component from the input signal, said harmonic being subsequently applied to the input of the amplitude detector 14. The rejection filter 6 and the tuneable filters 12 and 13 are tuned in synchronism with the variable-frequency harmonic signal generator 18. The detected signal comes to the first input of the first comparison unit 15 whose second input is fed with voltage from the output of the harmonic vibration level setter 19. From the output of the first comparison unit 15 an error signal is applied to the control input of the controllable divider 16 whose main (signal) input accepts a sum signal from the output of the third adder 17, the first input of which receives a harmonic signal from the output of the harmonic signal generator 18, the second input thereof being fed with calibrated DC voltage, $U_o$, from the output of the reference signal source 25. From the first output of the controllable divider 16 the signal representing the sum of harmonic and DC voltages is applied to the first input of the second comparison unit 20, the amplitude of said voltages being determined by the scaling ratio of the controllable divider 16, which is dependent upon an error signal derived from the output of the first comparison unit 15. From the second output of the controllable divider 16 the signal being an output signal harmonic component is fed to the second inputs of the second adder 7 and the second comparison unit 20. The controllable divider 16 is adjusted so that the level of harmonic vibrations of the vibrator 9 corresponds to a predetermined level. The output signal of the second comparison unit 20 being a DC component of a sum signal at the first output of the controllable divider 16 will change in much the same manner as an AC component at the second output of the controllable divider 16. Apparently, the magnitude of said signal will vary in accordance with the law $S_1(\omega)$ defined by the expression $$S_1(\omega) = U_o \frac{\beta}{\alpha(\omega)}, \qquad (I)$$

where $\alpha(\omega)$ is the amplitude-frequency response of the vibrator 9; and $\beta$ is a constant factor dependent on the level of suppression of a random signal at the output of the multichannel shaper by the tuneable rejection filter 6.

From the output of the second comparison unit 20 the signal is applied to the first input of the controllable amplifier 21 whose second input accepts the output signal of the reference signal source 25. A change of the gain of the controllable amplifier 21 is inversely proportional to that of the scaling ratio of the controllable divider 16. The output signal of the controllable amplifier 21 will vary in accordance with the law $S_2(\omega)$:

$$S_2(\omega) = U_o \frac{\alpha(\omega)}{\beta}.$$

This, the signal at the output of the controllable amplifier 21 unambiguously determines the amplitude-frequency response of the vibrator 9 in scanning a harmonic signal at the output of the generator 18. The output signal of the controllable amplifier 21 is applied through the squarer 22 to the input of the computer 23 whose second input receives data on the value of $q_i$ indicating spectral density of acceleration of vibrations at preset frequencies in a predetermined frequency range.

The computer 23 is preliminarily loaded with information on the amplitude-frequency response, $\varphi_n(\omega)$, of each channel comprised in the multichannel random signal shaper 1, said information conveying values of the amplitude-frequency response, $\varphi_n(\omega_i)$, at the specified frequencies.

Thereafter the computer 23 solves a set of equations of the form $$q_i = N_o \sum_{n=1}^{N} K_n{}^2 \varphi_n{}^2(\omega_i) \alpha^2(\omega_i), \qquad (II)$$

wherein $K_n$ is the gain of the adjustable amplifier 4 in the nth channel of the multichannel shaper I;

$N_o$ is the spectral density of a random signal at the output of each said white noise generator.

The output signals of the computer 23 set the gain of the adjustable amplifiers 4 according to the computed values of $K_n$, which determine the levels of random narrow-band signals in the channels of the multichannel shaper 1, the sum thereof forming a random wide-band signal which is used to produce random vibrations with preset values of $q_i$ indicating spectral density of acceleration of random vibrations at specified frequencies in a predetermined frequency range.

Computation of the gain, $K_n$, of the adjustable amplifiers 4 in the channels of the multichannel random signal shaper 1 involving the processing of a harmonic signal simultaneously used for testing articles with harmonic vibration increases accuracy and effectiveness of the tests.

Computing the gain of the adjustable amplifiers 4 in each channel of the multichannel random signal shaper 1 defining a spectrum of random vibrations affecting an article under test by solving the set of equations (II) permits utilizing low-order bandpass filters, that is, filters with a small squareness factor characterizing their amplitude-frequency responses, $\varphi_n(\omega)$, an advantage attributed to the fact that, in the present invention, account is taken of mutual effect of the bandpass filters 3 in said channels.

Turning now to FIG. 2 there is shown a functional diagram of the proposed system for testing articles with random and harmonic vibration. The system comprises the multichannel shaper 1 wherein each channel includes a noise generator 2 in which a primary noise source employs a zener diode 27 operating in the avalanche break-down mode. This mode is set by a resistor 28 placed between the cathode of the zener diode 27 and the collector of a transistor 29 which forms the amplifier in conjunction with a resistor 30. A capacitor 31 defines the lower frequency in the generated noise spectrum. A bus-bar 32 is used to feed power to the amplifier built around the transistor 29. The collector of the transistor 29 is connected to the input of the bandpass filter 3, more specifically, to an input resistor 33. The narrow-band filter 3 uses an operational amplifier 34. Resistors 33, 35 and capacitors 36, 37 define the tuning frequency of the bandpass filter 3. The output of the operational amplifier 34 is connected through a resistor 38 to the adjustable amplifier 4 using an operational amplifier 39. A photoresistor 40 inserted in the feedback circuit defines gain $K_n$ of the adjustable amplifier 4. The photoresistor 40 in conjunction with a light-emitting diode 41 represents a photon-coupled pair 42 contained within a single enclosure. The output of the adjustable amplifier 4 is connected to one of the inputs of the adder 5 using an operational amplifier 43 whose feedback circuit contains a resistor 44. Resistors 45 and 46 serves as input resistors of the adder 5.

The output of the operational amplifier 43 is connected to the input of the tuneable rejection filter 6 using an operational amplifier 47. The resistor 48 is an input resistor defining, in conjunction with a photoresistor 49 and capacitors 50, 51, the tuning frequency of the rejection filter 6. Resistors 52 and 53 define the gain of the operational amplifier 47 and the transmission band of the tuneable rejection filter 6. A photon-coupling pair 55 is formed by a light-emitting diode 54 in conjunction with a photoresistor 49. The cathode of the light-emitting diode 54 is connected to the control output of the variable-frequency harmonic signal generator 18.

The output of the operational amplifier 47 is connected to the first input of the second adder 7 using an operational amplifier 56 whose feedback circuit contains a resistor 57. Resistors 58 and 59 act as input resistors of the second adder 7.

The output of the operational amplifier 55 is connected to the input of the power amplifier 8 which is widely known in the art and is selected depending on the level of a desired vibration spectrum.

The output of the power amplifier 8 is connected to the input of the vibrator 9 whose particular embodiment is chosen to suit an article under test (not shown in the drawing). The vibration pick-up 10 to be mounted on said article is widely used in vibration tests and is normally a part of the vibrator 9. The output of the vibration pick-up 10 is connected to the input of the matching amplifier 11 commonly known in vibration tests, say, a Brüel & Kjaer Model 2626 (cf. brief catalogue "Devices for sound and vibration analysis and data processing", 1973, RS-22).

The output of the matching amplifier 11 is connected to the input of the second tuneable filter 12 using operational amplifiers 60 and 61. A resistor 62 serving as an input of the second tuneable filter 12 defines, in conjunction with a photoresistor 63 and capacitors 64, 65, the tuning frequency of a narrow-band tuneable filter 66 using the operational amplifier 60. A photon-coupled pair 68 is formed by a light-emitting diode 67 in conjunction with the photoresistor 63. The input of the second tuneable filter 12 is connected to a resistor 69, while the output of the operational amplifier 60 is connected to a resistor 70. The resistors 69 and 70 form two inputs of the adder using the operational amplifier 61 whose gain is defined by a resistor 71. The output of the operational amplifier 61 acting as the output of the second tuneable filter 12 is connected to the input of the first tuneable filter 13 which may be, for example, a heterodyne follow-up filter, Model 2021, manufactured by Brüel & Kjaer, Denmark. Said filter is tuned in response to a control signal from the output of the harmonic signal generator 18 (suitably the Model 1047 manufactured by the same firm in the preferred embodiment of the invention), the control output of which is also coupled to the light-emitting diodes 54 and 63, which makes it possible to tune, in synchronism with the harmonic signal generator 18, the rejection filter 6 and the second tuneable filter 12 having a reverse amplitude-frequency response with respect to the amplitude-frequency response of the rejection filter 6.

The harmonic signal output of the first tuneable filter 13 is connected to the input of the amplitude detector 14, more specifically, to the anode of a diode 72 whose cathode is connected to a resistor 73 which forms in conjunction with a capacitor 74 an integrating network with time constant $\tau = R_{73} \cdot C_{74}$. The output of the amplitude detector 14 formed by a common junction between the resistor 73 and the capacitor 74 is connected to the first input of the first comparison unit 15 using an operational amplifier 75 whose feedback circuit contains a resistor 76, more specifically, to a resistor 77.

The second input of the first comparison unit 15 is formed by a resistor 78 connected to the output of the harmonic vibration level setter 19 which may be a commonly known DC voltage source incorporating means for regulating an output signal level. The output of the operational amplifier 75 is connected to the first input of the controllable divider 16, more particularly, to the cathode of a light-emitting diode 79 which forms, in conjunction with a photoresistor 80, a photon-coupled pair 81. The controllable divider 16 is formed by connecting a resistor 82 to the photoresistor 80 whose value is conditioned by the glow of the light-emitting diode 79. The second input of the controllable divider 16 using the resistor 82 is connected to the output of the third adder 17 incorporating an operational amplifier 83 and resistors 84, 85, 86. The first input of the third adder 17 is the resistor 85 connected to the output of the variable-frequency harmonic signal generator 18, while the second input of the third adder 17 is formed by the resistor 86 connected to the reference voltage source 25. The first output of the controllable divider 16 formed by a capacitor 87 is connected to the second input of the second adder 7, more specifically, to the resistor 59 and to the first input of the second comparison unit 20, more particularly, to a resistor 88, while the second output of the controllable divider 16 (the junction between the resistor 82 and the capacitor 87) is connected to the second input of the comparison unit 20, more specifically, to a resistor 89.

The second comparison unit 20 is formed by an operational amplifier 90 and resistors 88, 89, 91.

The output of the operational amplifier 90 is connected to a light-emitting diode 92 acting as the first input of the controllable amplifier 21. The second input of the controllable amplifier 21 formed by a photoresistor 93 constituting a photon-coupled pair 94 in conjunction with the light-emitting diode 92 is connected to the output of the reference voltage source 25 which may be a widely known regulated DC voltage source with a percent ripple equal to 3–5%. The controllable amplifier 21 uses an operational amplifier 95 whose feedback circuit contains a resistor 96. The gain of the controllable amplifier 21 is conditioned by the changing glow of the light-emitting diode 92. The output of the operational amplifier 95 is connected to the input of the squarer 22 having a square amplitude characteristic. The squarer 22 may use the circuitry described by J.-C. Marchais in "L'AMPLIFICATEUR OPERATIONNEL ET SES APPLICATIONS", MASSON at Cie, EDITEURS, PARIS, 1971.

The output of the squarer is connected to the input of the computer 23 and the indicator 26. The computer 23 may be the Model 7504 manufactured by the above firm (cf. the afore-mentioned catalog). The random vibration spectrum indicator 26 may be, for example, a cathode-ray tube. Connected to the second input of the computer 23 is the output of the unit 24 setting the random vibration spectrum as values of $q_i$ indicating spectral density of acceleration of vibration at preset frequencies in a predetermined frequency range. The random vibration spectrum setter 24 may be a Model 6401 teleprinter manufactured by the same firm.

The output of the computer 23 is connected to the light-emitting diodes 41 of the adjustable amplifiers 4 in each channel I and II of the multichannel random signal shaper I.

The proposed system for testing random and harmonic vibration operates in the following manner.

A random wide-band signal derived from the output of the noise generator 2 in channel I and II of the multichannel random signal shaper 4, more specifically, from the collector of the transistor 29 is applied to the input resistor 33 of the bandpass filter 3 which discriminates only those spectral components in the entire input spectrum, which are within its transmission band. The midband frequency of the transmission band is determined by the values of the resistors 33, 35 and the capacitors 36, 37. The transmission band is also dependent upon the gain of the operational amplifier 34. From the output of the operational amplifier 34 a random narrow-band signal comes to the input of the adjustable amplifier 4, more particularly, through the input resistor 38 to the input of the operational amplifier 39 whose gain is determined by the value of the photoresistor 40, which, in turn, is conditioned by the glow of the light-emitting diode 41. The output signals of the operational amplifiers 39 in channels I and II come to the adder 5, that is, to the input of the operational amplifier 43 through the input resistors 45 and 46, respectively.

From the output of the operational amplifier 43 a sum random signal of two narrow-band channels I and II comes to the resistor 48. The amplitude-frequency response of the tuneable filter 6 is the amplitude-frequency response of the rejection filter, the rejection frequency being tuned to suit the changing value of the photoresistor 49. The value of the photoresistor 49 is, in turn, conditioned by the glow of the light-emitting diode 54 whose cathode receives a control voltage from the control output of the variable-frequency harmonic signal generator 18. Thus, the tuneable rejection filter 6 is tuned in synchronism with the harmonic signal generator 18. In this case no rejection frequencies will be present at the output of the tuneable rejection filter 6 in the signal spectrum. From the output of the operational amplifier 47 the signal is fed to the first input of the second adder 7 whose second input receives the signal from the input of the variable-frequency harmonic signal generator 18 through the third adder 17 and the controllable divider 16. Thus, a sum of random and harmonic signals will be present at the output of the second adder 7, the frequency of the variable-frequency harmonic signal being coincident with the random signal rejection frequency over the entire range. From the output of the operational amplifier the sum signal is fed through the power amplifier 8 to the input of the vibrator 9, thereby producing random and harmonic vibrations in the vibrating table thereof. The output signal of the vibration pickup 10 is applied through the matching amplifier 11 to the input of the second tuneable filter 12 having a reverse amplitude-frequency response with respect to the amplitude-frequency response of the tuneable rejection filter 6. This is done by summing up a narrow-band signal from the output of the tuneable narrow-band filter 66 built around the operational amplifier 60 and the output signal of the matching amplifier 11. The tuneable narrow-band filter is tuned in synchronism with the harmonic signal generator 18 by changing the value of the photoresistor 63. The value of the photoresistor 63 is conditioned by the glow of the light-emitting diode 67, the cathode of which is fed with the control voltage from the control output of the variable-frequency harmonic signal generator 18. From the output of the second tuneable filter the signal representing a sum of a wide-band random signal and a harmonic signal amplified by many times is applied to the input of the first tuneable filter 13 which extracts a harmonic component from the input signal, said component being applied to the input of the amplitude detector 14. The signal from the capacitor 74 in the form of a positive DC voltage is applied to the first input of the first comparison unit 15, that is, to the resistor 77. The second input of the first comparison unit 15, that is, the resistor 78 receives negative voltage from the output of the harmonic vibration lever setter 19. A differential signal from the output of the operational amplifier 75 is applied to the input of the controllable divider 16, more specifically, to the light-emitting diode 79. The value of the photoresistor 80 changes depending on the glow of the light-emitting diode 79. The second input of the controllable divider 16, namely the resistor 82, accepts a sun of a variable-frequency harmonic signal and DC voltage $U_o$, said sum signal being applied from the output of the third adder 17. The harmonic signal arrives at the first input of the third adder 17, that is, to the resistor 85, said signal being applied from the output of the variable-frequency harmonic signal generator 18, while the DC voltage, $U_o$, comes to the second input of the third adder 17, that is, to the resistor 66, said voltage being furnished by the reference voltage source 25.

The resistor 82 and the photoresistor 80 form the controllable divider 16, a harmonic signal of an amplifier varying in frequency in inverse proportion to the amplitude-frequency response of the vibrator being amplified to the second input of the second adder 7 and to the first input of the second comparison unit 20, more specifically, to the resistor 88. The second input of the second comparison unit 20, more particularly, the resistor 89 accepts a sum of the harmonic signal and the DC voltage from the second output of the controllable divider 16, more particularly, from the resistor 82, the amplitude of said voltage varying also in inverse proportion to the amplitude-frequency response of the vibrator. The output of the operational amplifier 90 will develop only DC voltage whose amplitude changes in inverse proportion to the amplitude-frequency response $\alpha(\omega)$ of the vibrator 9 when the harmonic signal frequency is tuned. The output signal of the operational amplifier 90 is applied to the light-emitting diode 92. The value of the photoresistor 93 and, consequently, the gain of the controllable amplifier 21 will vary in direct proportion to the amplitude-frequency response $\alpha(\omega)$ of the vibrator 9.

So, the output signal of the operational amplifier 95 unambiguously defines the amplitude-frequency response $\alpha(\omega)$ of the vibrator 9 when the frequency of the harmonic signal is changed. The output signal of the operational amplifier 93 is applied to the squarer 22, the output signal thereof proportional to the square of the amplitude-frequency response $\alpha(\omega)$ of the vibrator 9 being fed to the input of the indicator 26 and to the input of the computer 23 whose other input receives the values of $q_i$ indicating spectral density of acceleration of vibrations at preset frequencies in a predetermined frequency range, said data coming from the random vibration spectrum setter 24. The computer 23 is preliminarily loaded with information on the amplitude-frequency response $\varphi_n(\omega)$ of each channel of the multichannel random signal shaper 1, said information conveying the values of the amplitude-frequency response $\varphi_n(\omega_i)$ at the specified frequencies.

Thereafter the computer 23 solves the set of equations of the form $$q_i = N_o \sum_{n=1}^{N} K_n^2 \varphi_n^2(\omega_i) a^2(\omega_i), \qquad (II)$$

where $K_n$ is the gain of the adjustable amplifier in the nth channel of the multichannel shaper 1.

The output signals of the computer 23 set the gain of the adjustable amplifiers 4 according to the obtained values of $K_n$. The values of $K_n$ define the levels of narrow-band random signals in the channels of the multichannel shaper 1, the sum thereof yielding a wide-band random signal used to produce random vibrations with preset values of $q_i$ indicating spectral density of acceleration of random vibrations at preset frequencies $\omega_i$ in a predetermined frequency range.

What is claimed is:

1. A system for testing articles with random and harmonic vibration comprising:

a multichannel random signal shaper having several channels, each channel having an intrinsic amplitude-frequency response and including:

a white noise generator;

a bandpass filter connected to said white noise generator;

an adjustable amplifier having two inputs and an output, the first input being connected to said bandpass filter; a first adder having several inputs whose number corresponds to the number of said channels and an output, said inputs of said adder being connected to the outputs of said adjustable amplifiers of the respective channels;

a tuneable rejection filter having two inputs and an output, the first input being connected to the output of said first adder;

a second adder having two inputs and an output, the first input being connected to said output of said tuneable rejection filter;

a power amplifier connected to the output of said second adder;

a vibrator connected to the output of said power amplifier;

a vibration pick-up mounted on the vibrator;

a matching amplifier connected to said vibration pick-up;

a second tuneable filter having a reverse amplitude-frequency response with respect to an amplitude-frequency response of said tuneable rejection filter and provided with two inputs and an output, the first input being connected to said matching amplifier;

a first tuneable filter having two inputs and a harmonic signal output and a suppression output, the first input being connected to said output of said second tuneable filter;

a variable-frequency harmonic signal generator having a signal output and a control output, said control output being connected to said second input of said rejection filter, to said second input of the first tuneable filter and to said second input of the second tuneable filter to enable synchronous tuning thereof;

a random vibration spectrum analyzer connected to said suppression output of the first tuneable filter, the output of said analyzer being connected to the second input of said adjustable amplifier in each channel.

2. A system as claimed in claim 1, wherein the random vibration spectrum analyzer is a harmonic signal analyzer comprising:

an amplitude detector connected to the first output of said first tuneable filter;

a first comparison unit having two inputs and an output, the first input being connected to said amplitude detector;

a harmonic vibration level setter connected to the second input of said first comparison unit;

a third adder having two inputs and an output, the first input being connected to said signal output of said variable-frequency harmonic signal generator;

a controllable divider having two inputs and a sum signal output and a signal AC component output, the first input being connected to said output of the first comparison unit, the second input being connected to said output of the third adder, while the signal AC component output is connected to the second input of the second adder;

a second comparison unit having two inputs and an output, the first input being connected to said signal AC component output of said controllable divider, the second input of the second comparison being connected to said sum signal output of said controllable divider;

a controllable amplifier whose gain is inversely proportional to the attentuation factor of said controllable amplifier, said controllable amplifier having two inputs and an output, the first input being connected to said output of the second comparison unit;

a squarer having a square amplitude-frequency response and connected to said output of said controllable amplifier;

a random vibration spectrum indicator connected to said squarer;

a reference voltage source having its output connected to the second input of the third adder and to the second input of said controllable amplifier;

a computer having two inputs and an output, the first input being connected to said output of said squarer, while the output is connected to said second input of said adjustable amplifier in each channel of said multichannel random signal shaper;

a random vibration spectrum setter connected to the second input of said computer.

3. A system as claimed in claim 2, wherein gain of said adjustable amplifiers is determined by solving a set of the following equations using said computer:

$$q_i = N_o \sum_{n=1}^{N} K_n{}^2 \varphi_n{}^2(\omega_i) a^2(\omega_i),$$

where $q_i$ is a preset spectral density of acceleration of random vibrations at the ith frequency in a predetermined frequency range;

$a(\omega_i)$ is the measured amplitude-frequency response of the vibrator at said ith frequency in said frequency range;

$K_n$ is gain of said adjustable amplifier in the nth channel of said multichannel random signal shaper;

$\varphi_n(\omega_i)$ is the amplitude-frequency response of the nth channel at said ith frequency in said frequency range; and $N_o$ is spectral density of a random signal at the output of each white noise generator.

4. A system for testing articles with random and harmonic vibration comprising:

(a) a power supply;

(b) a multichannel random signal shaper having several channels, each channel including:

a white noise generator composed of:

a capacitor having one grounded lead;

a zener diode whose cathode is connected to the second lead of said capacitor;

a transistor having its base connected to the anode of said zener diode, an emitter of said transistor being adequately grounded;

a first resistor inserted between the cathode of said zener diode and the collector of said transistor;

a second resistor having one lead thereof connected to the collector of said transistor and its second lead connected to said power supply;

a bandpass filter composed of:

a first resistor having one lead thereof connected to the collector of said transistor;

a first capacitor having one lead connected to the second lead of said first resistor;

a second capacitor having one lead also connected to said second lead of said first resistor;

a second resistor inserted between the second lead of said first capacitor and the second lead of said capacitor;

an operational amplifier having an inverting input and a noninverting input, the inverting input being suitably grounded, while the noninverting input is connected to said second lead of said first capacitor;

an adjustable amplifier comprising:

a resistor connected to the output of said operational amplifier;

another operational amplifier also having an inverting input and a noninverting input, the inverting input being suitably grounded, while the noninverting input is connected to said resistor;

a photoresistor inserted between the noninverting input of said other operational amplifier and its output;

a light-emitting diode lighting said photoresistor and forming therewith a photon-coupled pair, one lead of the light-emitting diode being adequately grounded;

(c) a first adder comprising:

several input resistors whose number corresponds to the number of said channels, first leads of said input resistors being connected to the outputs of said operational amplifiers in each adjustable amplifier, second leads of said input resistors being suitable interconnected;

an operational amplifier having an inverting input and a noninverting input, the inverting input being suitably grounded, while the noninverting input is connected to said second leads of said second resistors;

a resistor inserted between said noninverting input of said operational amplifier and its output;

(d) a tuneable rejection filter comprising:

a first resistor having its first lead connected to the output of said operational amplifier of said first adder;

a first capacitor having one lead thereof connected to said first lead of said first resistor;

a second capacitor having one lead thereof connected to the second lead of said first resistor;

an operational amplifier having an inverting input and a noninverting input, the inverting input being connected to said second lead of said first resistor;

a photoresistor inserted between the inverting input of said operational amplifier and its output;

a light-emitting diode lighting said photoresistor and forming therewith a photon-coupled pair, one lead of the light-emitting diode being adequately grounded;

a second resistor inserted between the noninverting input of said operational amplifier and its output;

a third resistor, one lead of which is grounded, while the other lead thereof is connected to the noninverting input of said operational amplifier;

(e) a second adder comprising:

a first resistor having one lead thereof connected to the output of said operational amplifier of said tuneable rejection filter;

a second resistor, one lead of which is connected to the other lead of said first resistor;

an operational amplifier having an inverting input and a noninverting input, the inverting input being suitably grounded, while the noninverting input is connected to said second lead of said first resistor;

a third resistor inserted between the noninverting input of said operational amplifier and its output;

(f) a power amplifier connected to the output of said operational amplifier of said second adder;

(g) a vibrator with a vibration pick-up connected to said power amplifier;

(h) a matching amplifier connected to said vibration pick-up;

(i) a second tuneable filter having a reverse amplitude-frequency response with respect to the amplitude-frequency response of said tuneable rejection filter and comprising:

a narrow-band tuneable filter composed of:

a first resistor, one lead of which is connected to said matching amplifier;

a first capacitor, one lead of which is connected to the other lead of said first resistor;

an operational amplifier having an inverting input and a noninverting input, the inverting input being suitable grounded, while the noninverting input is connected to the other lead of said first capacitor;

a photoresistor inserted between the noninverting input of said operational amplifier and its output;

a light-emitting diode lighting said photoresistor and forming therewith a photon-coupled pair, one lead of said light-emitting diode being suitably grounded;

a second capacitor inserted between the first lead of said first capacitor and the output of said operational amplifier;

(j) an adder comprising:

a first resistor, one lead of which is connected to the output of said operational amplifier of the narrow-band tuneable filter;

a second resistor, one lead of which is connected to said matching amplifier;

an operational amplifier having an inverting input and a noninverting input, the inverting input being suitably grounded, the noninverting input being connected to the second leads of said first and second resistors, which are interconnected;

a third resistor inserted between the noninverting input of said operational amplifier and its output;

a first tuneable filter having two inputs, the first input being connected to the output of said operational amplifier of said adder of said second tuneable filter;

(k) an amplitude detector comprising:

a diode having its cathode connected to the output of said first tuneable filter;

a resistor, one lead of which is connected to the anode of said diode;

a capacitor, one lead of which is suitably grounded, while the other lead thereof is connected to the second lead of said resistor;

(l) a first comparison unit incorporating:

a first resistor, one lead of which is connected to said second lead of said resistor of said amplitude detector;

an operational amplifier having an inverting input and a noninverting input, the inverting input being suitably grounded, while the noninverting input is connected to the second lead of said first resistor;

a second resistor inserted between the noninverting input of said operational amplifier and its output;

a third resistor, one lead of which is connected to said second lead of said first resistor;

(m) a harmonic vibration level setting unit connected to the other lead of said third resistor of said first comparison unit;

(n) a variable-frequency harmonic signal generator having a signal output and a control output, said control output being connected to said second input of said first tuneable filter, to the second lead of said light-emitting diode of the tuneable rejection filter and to the second lead of said second tuneable filter;

(o) a third adder comprising:

a first resistor, one lead of which is connected to said signal output of said variable-frequency random signal generator;

an operational amplifier having an inverting input and a noninverting input, the noninverting input being connected to the second lead of said first resistor;

a second resistor inserted between the noninverting input of said operational amplifier and its output;

a third resistor, one lead of which is connected to the noninverting input of said operational amplifier;

(p) a controllable divider comprising:

a photoresistor having one grounded lead;

a light-emitting diode lighting the photoresistor and forming in conjunction therewith a photon-coupled pair, one lead of said light-emitting diode being grounded, while the other lead thereof is connected to the output of said operational amplifier of said first comparison unit;

a resistor, one lead of which is connected to the output of said operational amplifier of said third adder, the other lead of said resistor being connected to the second lead of said photoresistor;

a capacitor, one lead of which is connected to said second lead of said resistor, while the other lead of said capacitor is connected to the second lead of said second resistor of said second adder;

(q) a second comparison unit comprising:

a first resistor, one lead of which is connected to said second lead of said capacitor of said controllable divider;

a second resistor, one lead of which is connected to said second lead of said resistor of said controllable divider;

an operational amplifier having an inverting input and a noninverting input, the inverting input being connected to the second lead of said second resistor, while the noninverting input is connected to the other lead of said first resistor;

a third resistor inserted between the non-inverting input of said operational amplifier and its output;

(r) a reference voltage source connected to the other lead of said third resistor of said third adder;

(s) a controllable amplifier comprising:

a photoresistor, one lead of which is connected to said reference voltage source;

a light-emitting diode lighting said photoresistor and forming therewith a photon-coupled pair, one lead of the light-emitting diode being suitably grounded, while the other lead thereof is connected to the output of said operational amplifier of said second comparison unit;

an operational amplifier having an inverting input and a noninverting input, the inverting input being suitably grounded, while the noninverting input is connected to the other lead of said photoresistor;
a resistor inserted between the noninverting input of said operational amplifier and its output;
(t) a squarer connected to the output of said operational amplifier of said controllable amplifier;
(u) a random vibration spectrum indicator connected to said squarer;
(v) a computer having two inputs and an output, the first input being connected to said squarer, while the output thereof is connected to the other lead of said light-emitting diode of each adjustable amplifier of said multichannel random signal shaper;
(w) a random vibration spectrum setter connected to said second input of said computer.

* * * * *